US009398974B1

(12) United States Patent
DelRio et al.

(10) Patent No.: US 9,398,974 B1
(45) Date of Patent: Jul. 26, 2016

(54) BRUXISM SENSOR

(71) Applicants: Eddy H. DelRio, Royal Palm Beach, FL (US); Connie Lee DelRio, Royal Palm Beach, FL (US)

(72) Inventors: Eddy H. DelRio, Royal Palm Beach, FL (US); Connie Lee DelRio, Royal Palm Beach, FL (US)

( * ) Notice: Subject to any disclaimer, the term of this patent is extended or adjusted under 35 U.S.C. 154(b) by 0 days.

(21) Appl. No.: 14/618,706

(22) Filed: Feb. 10, 2015

(51) Int. Cl.
*A61F 5/56* (2006.01)

(52) U.S. Cl.
CPC ........... *A61F 5/566* (2013.01); *A61F 2005/563* (2013.01)

(58) Field of Classification Search
CPC ..... A61F 5/56; A61F 2005/563; A61F 5/566; G01F 1/22; G01F 1/24; G01F 1/34; G01F 1/37; G01L 7/08; A61B 5/4557; A61B 5/228; A61B 5/682; A61B 71/085; A61C 5/14; A61C 7/08
USPC .......... 200/83 S, 83 SA; 340/611, 626; 433/6
See application file for complete search history.

(56) References Cited

U.S. PATENT DOCUMENTS

| 2,834,845 | A | * | 5/1958 | Nielsen | F04D 15/0218 200/81.5 |
|---|---|---|---|---|---|
| 4,262,289 | A | * | 4/1981 | Rivera | G01V 1/008 200/61.51 |
| 4,976,618 | A | * | 12/1990 | Anderson | A61C 19/04 433/215 |
| 4,995,404 | A | | 2/1991 | Nemir | |
| 5,078,153 | A | | 1/1992 | Nordlander et al. | |
| 5,586,562 | A | | 12/1996 | Matz | |
| 5,921,241 | A | * | 7/1999 | Belfer | A61F 5/566 128/848 |
| 6,093,158 | A | | 7/2000 | Morris | |
| 2003/0234727 | A1 | | 12/2003 | Perlman | |
| 2009/0120446 | A1 | | 5/2009 | Vaska et al. | |
| 2009/0288241 | A1 | * | 11/2009 | Fullerton | A41D 13/1161 2/421 |

\* cited by examiner

*Primary Examiner* — Victoria J Hicks
*Assistant Examiner* — Michelle J Lee
(74) *Attorney, Agent, or Firm* — Jetter & Associates, P.A.

(57) ABSTRACT

A bruxism sensor includes a diaphragm switch which provides an electrical output including a diaphragm separating a pressure side having a pressure side inlet and a suction side having a suction side inlet. An audible alarm having an electrical input is coupled to the electrical output. A first hose has one end is fluidically coupled to the pressure side inlet and a biting configured opposite end (biting end) for positioning between teeth of a user. Wherein upon a contraction of a mandible of the user, the biting end is squeezed which generates air pressure that is applied to the pressure side to generate a pressure level sufficient for activating the diaphragm switch, and while the diaphragm switch is activated, the audible alarm automatically sounds an alarm for alerting the user of contraction of their mandible.

7 Claims, 3 Drawing Sheets

BRUXISM SENSOR

FIELD

Disclosed embodiments relate to bruxism sensors.

BACKGROUND

Bruxism is defined as the excessive grinding of the teeth and/or excessive clenching of the jaw of an individual being unrelated to normal human functions such as eating or talking. Bruxism may cause minimal symptoms, and therefore individuals may not be aware of the condition. Symptoms commonly associated with bruxism include hypersensitive teeth, aching jaw muscles, and headaches. Bruxism can cause tooth wear, and can in extreme cases damage or break teeth and dental restorations such as crowns and fillings.

Bruxism can occur during sleep (sleep bruxism) and during waking hours (awake bruxism). Dental damage may be similar in both types, but the symptoms of sleep bruxism tend to worsen on waking and improve during the course of the day, and the symptoms of awake bruxism may not be present at all on waking, and then worsen over the course of the day. Several bruxism treatments are known, which generally all include a powered sensor device.

SUMMARY

This Summary is provided to introduce a brief selection of disclosed concepts in a simplified form that are further described below in the Detailed Description including the drawings provided. This Summary is not intended to limit the claimed subject matter's scope.

A bruxism sensor includes a diaphragm switch which provides an electrical output that includes a diaphragm separating a pressure side having a pressure side inlet and a suction side having a suction side inlet. An audible alarm having an electrical input is coupled to the electrical output of the diaphragm switch A first hose has one end is fluidically coupled to the pressure side inlet and a biting configured opposite end (biting end) for positioning between teeth of a user. Upon a contraction of a mandible of the user, the biting end is squeezed which generates air pressure that is applied to the pressure side input which generates a pressure level sufficient for activating the diaphragm switch. While the diaphragm switch is activated, the audible alarm automatically sounds an alarm for alerting the user of contraction of their mandible.

BRIEF DESCRIPTION OF THE DRAWINGS

Reference will now be made to the accompanying drawings, which are not necessarily drawn to scale, wherein.

DETAILED DESCRIPTION

Figure 1:
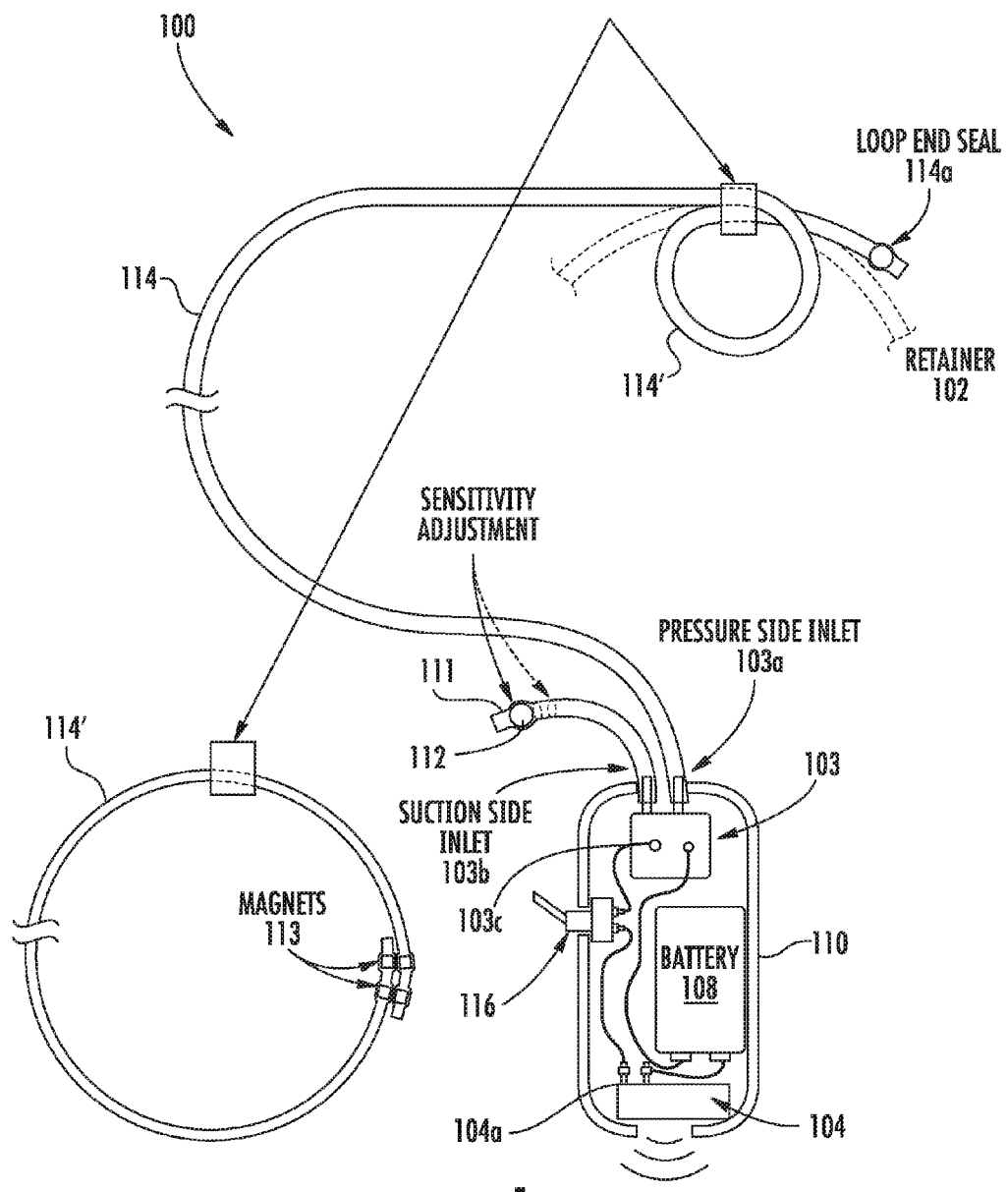
FIG. 1 is a depiction of an example bruxism sensor, according to an example embodiment.

Disclosed embodiments in this Disclosure are described with reference to the attached figures, wherein like reference numerals are used throughout the figures to designate similar or equivalent elements. The figures are not drawn to scale and they are provided merely to illustrate the disclosed embodiments. Several aspects are described below with reference to example applications for illustration. It should be understood that numerous specific details, relationships, and methods are set forth to provide a full understanding of the disclosed embodiments.

One having ordinary skill in the relevant art, however, will readily recognize that the subject matter disclosed herein can be practiced without one or more of the specific details or with other methods. In other instances, well-known structures or operations are not shown in detail to avoid obscuring structures or operations that are not well-known. This Disclosure is not limited by the illustrated ordering of acts or events, as some acts may occur in different orders and/or concurrently with other acts or events. Furthermore, not all illustrated acts or events are required to implement a methodology in accordance with this Disclosure.

Notwithstanding that the numerical ranges and parameters setting forth the broad scope of this Disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5.

FIG. 1 is a depiction of an example bruxism sensor 100, according to an example embodiment. Bruxism sensor 100 includes a pressure-sensitive diaphragm switch (diaphragm switch) 103 which provides an electrical output 103c that includes a flexible diaphragm (see diaphragm 103d in FIG. 2) for separating a pressure side 103a' having a pressure side inlet 103a and a suction side 103b' including a suction side inlet 103b. An audible alarm 104 having an electrical input 104a such as a buzzer is electrically coupled to the electrical output 103c of the diaphragm switch 103. A battery 108 is shown within a case 110 for the diaphragm switch 103 and alarm 104 which provides power to the diaphragm switch 103 and audible alarm 104. Alternatively, an electrical plug can be provided to enable power to be received from an external power source (e.g., power company source). An optional on-off switch 116 is also shown. The diaphragm switch 103, on-off switch 116 and audible alarm 104 can be seen to be configured in a series circuit with the battery 108 being the power source for the series circuit. In one embodiment the battery is a 9 V DC battery. The diaphragm switch 103, on-off switch 116, audible alarm 104, and battery 108 can all be off-the-shelf commercially available components. The on-off switch 116 is optional as the diaphragm switch 103 when non-activated keeps the series circuit in an open-circuit condition.

A first hose 114 has one end fluidically coupled to the pressure side inlet 103a of the diaphragm switch 103 and a biting configured opposite end (biting end) 114' shown configured as a sensor loop for positioning between teeth of a user. The first hose 114 and other hoses described herein generally comprise small diameter flexible plastic hose, such as air hoses used for aquariums. Other biting end 114' configurations are possible, including a pacifier shape.

Upon a contraction of a mandible of the user the biting end 114', air pressure is generated that is applied to the pressure side of the diaphragm switch 103 via the pressure side inlet 103a to a pressure level sufficient for displacing the diaphragm for activating (turning on) the diaphragm switch 103. While the diaphragm switch 103 is activated, the audible alarm 104 shown as a buzzer sounds an alarm for alerting the user of contraction of the mandible during sleep. Unlike conventional bruxism sensors, the biting end 114' is an entirely passive bite sensor and thus does not need any power supplied to it.

The bruxism sensor 100 is shown also including a second hose 111 coupled to the suction side inlet 103b including a cavity volume modulator 112 shown as a bee bee for changing the back pressure that can be used for adjusting a sensitivity of the diaphragm switch 103. As the cavity volume modulator 112 is moved by the user further from the suction side inlet 103b the cavity volume of the diaphragm switch 103 decreases which increases the sensitivity of diaphragm switch 103, and as the cavity volume modulator 112 is moved by the user closer to the suction side inlet 103b the cavity volume of the diaphragm switch 103 increases which decreases the sensitivity of diaphragm switch 103. The bruxism sensor 100 is also shown including a retainer or harness 102 sized and shaped to fit over a head of the user for supporting the biting end 114' of the first hose 114 which includes a loop end seal 114a such as a bee bee. Magnets 113 are shown for providing a magnetic latch for the retainer or harness 102. Significant advantages of bruxism sensor 100 include an entirely passive sensing mechanism that operates without need for a power source as the contraction of the mandible of the user provides the pressured air flow used for turning on the diaphragm switch 103.

Figure 2:
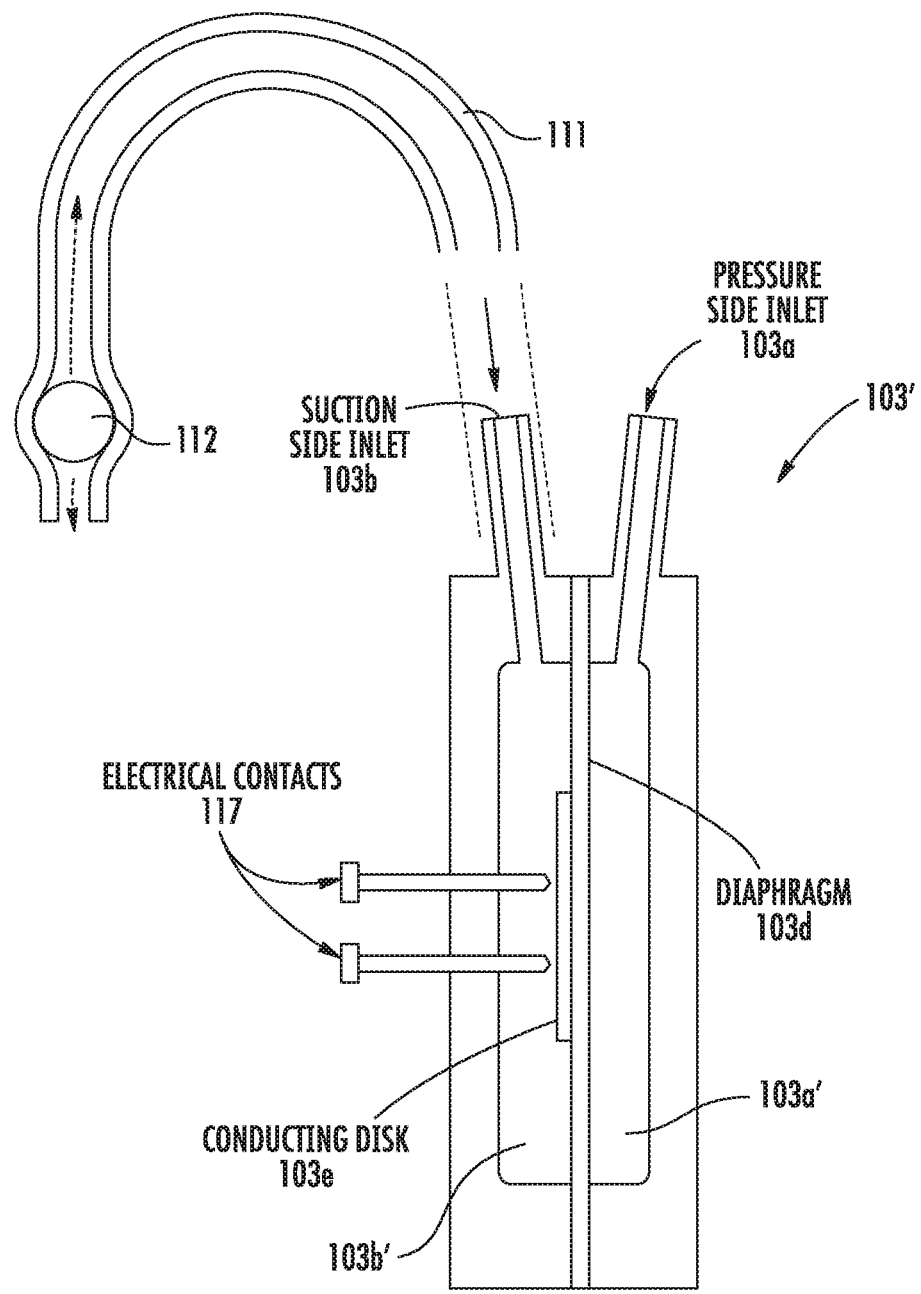
FIG. 2 is a depiction over an example diaphragm switch, according to an example embodiment.

FIG. 2 is a depiction over an example diaphragm switch shown as 103', according to an example embodiment. The flexible diaphragm 103d is shown separating the pressure side and the suction side of the diaphragm switch 103. An electrically conducting disk 103e is on the flexible diaphragm 103d. Upon sufficient differential pressure being applied across the diaphragm 103d responsive to contraction of the mandible of the user, the electrically conducting disk 103e is displaced sufficiently to contact the electrical contacts 117 shown which activates the diaphragm switch 103.

Figure 3:
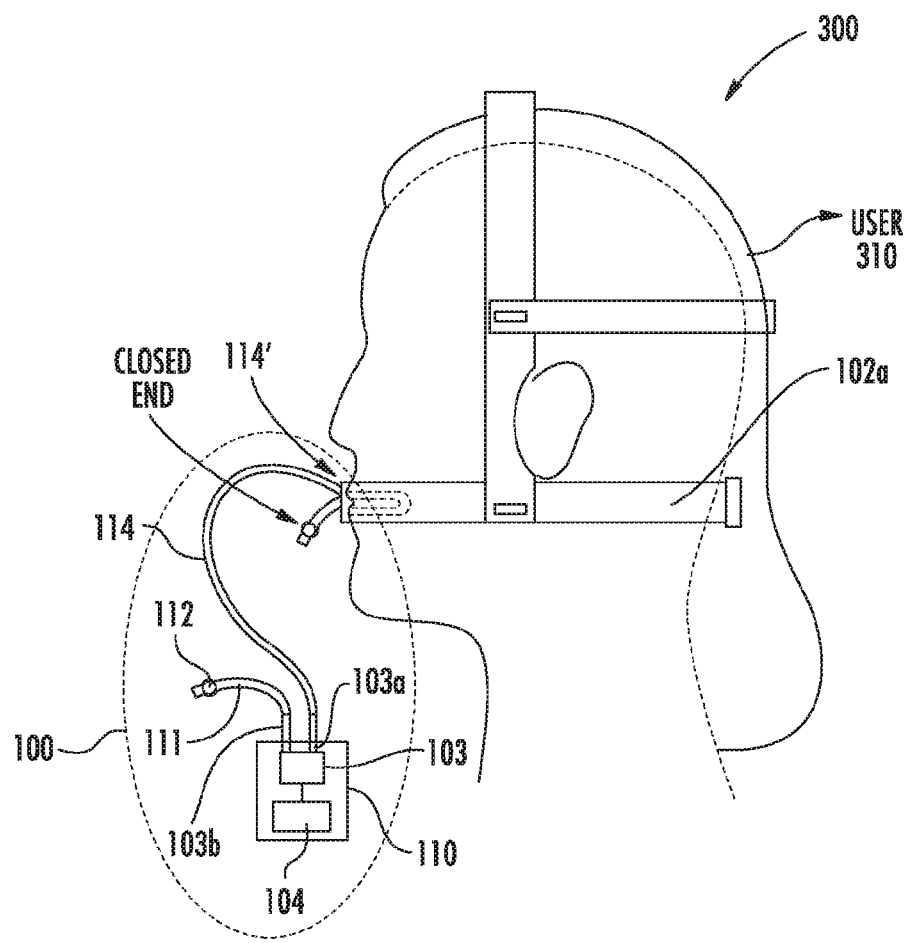
FIG. 3 is a depiction showing the example bruxism sensor shown in FIG. 1 positioned on the head of a user for sensing contraction of a mandible of the user and sounding an alarm for alerting the user of contraction of their mandible, according to an example embodiment.

FIG. 3 is a depiction 300 showing the example bruxism sensor 100 positioned on the head of a user 310 for sensing contraction of a mandible of the user and sounding an alarm for alerting the user of contraction of their mandible, according to an example embodiment. The biting end 114' shown as a sensor loop includes a distal closed end, provided by the bee bee shown, or by another suitable flow obstruction. The closed end results in contraction of the user's mandible directing essentially all the air flow generated toward the diaphragm switch 103. The retainer or harness is shown as 102a.

Disclosed embodiments include methods of treating bruxism. A biting end of a first hose is placed between teeth of a user having another end coupled to a pressure side inlet of a pressure side of a diaphragm switch which provides an electrical output including a diaphragm separating The pressure side and a suction side having a suction side inlet, wherein an audible alarm which has an electrical input is coupled to the electrical output of the diaphragm switch. Upon a contraction of a mandible of the user, the biting end of the first hose is squeezed which generates air pressure that is applied to the pressure side to provide a pressure level sufficient for activating the diaphragm switch, and while the diaphragm switch is activated, an audible alarm is automatically sounded to awaken the user of the contraction of their mandible.

While various disclosed embodiments have been described above, it should be understood that they have been presented by way of example only, and not limitation. Numerous changes to the subject matter disclosed herein can be made in accordance with this Disclosure without departing from the spirit or scope of this Disclosure. In addition, while a particular feature may have been disclosed with respect to only one of several implementations, such feature may be combined with one or more other features of the other implementations as may be desired and advantageous for any given or particular application.

Thus, the breadth and scope of the subject matter provided in this Disclosure should not be limited by any of the above explicitly described embodiments. Rather, the scope of this Disclosure should be defined in accordance with the following claims and their equivalents.

The invention claimed is:

1. A bruxism sensor, comprising:
 a diaphragm switch including a diaphragm separating a pressure side having a pressure side inlet and a suction side including an electrically conductive surface on exclusively a center portion of said diaphragm that is spaced apart from electrical contacts including a second hose coupled to a suction side inlet;
 an audible alarm having an electrical input coupled to said electrical contacts;
 a first hose having one end fluidically coupled to said pressure side inlet, and a biting configured opposite end (biting end) for positioning between teeth of a user;
 a restriction in said second hose that closes said second hose to an atmosphere to define a cavity volume for said suction side;
 wherein upon a contraction of a mandible of said user:
  said biting end is adapted to be squeezed which generates air pressure that is applied to said pressure side to generate a pressure level sufficient for moving said diaphragm so that said electrically conductive surface contacts said electrical contacts for activating said diaphragm switch, and
  while said diaphragm switch is activated, causing said audible alarm to automatically sound an alarm adapted for alerting said user of said contraction of said mandible.

2. The bruxism sensor of claim 1, further comprising an on-off switch between said electrical input of said audible alarm and said electrical contacts.

3. The bruxism sensor of claim 2, further comprising a battery within a case of said diaphragm switch coupled to provide power to said on-off switch, said audible alarm and said diaphragm switch.

4. The bruxism sensor of claim 1, further comprising a harness adapted to be fit over a head of said user for supporting said biting end.

5. The bruxism sensor of claim 4, further comprising a plurality of magnets adapted for securing said biting end around said user's head.

6. The bruxism sensor of claim 1, wherein said biting end comprises a loop.

7. The bruxism sensor of claim 1, wherein said restriction comprises an adjustable cavity volume modulator for changing said cavity volume to adjust a sensitivity of said diaphragm switch.

* * * * *